(12) United States Patent
Shibata et al.

(10) Patent No.: US 10,676,439 B2
(45) Date of Patent: Jun. 9, 2020

(54) PENTAFLUOROSULFANYL PYRIDINE

(71) Applicant: UBE INDUSTRIES, LTD., Yamaguchi (JP)

(72) Inventors: Norio Shibata, Aichi (JP); Kohei Matsuzaki, Aichi (JP); Norimichi Saito, Yamaguchi (JP)

(73) Assignee: UBE INDUSTRIES, LTD. (JP)

( * ) Notice: Subject to any disclaimer, the term of this patent is extended or adjusted under 35 U.S.C. 154(b) by 0 days.

(21) Appl. No.: 15/778,920

(22) PCT Filed: Nov. 25, 2016

(86) PCT No.: PCT/JP2016/085036
§ 371 (c)(1),
(2) Date: May 24, 2018

(87) PCT Pub. No.: WO2017/090746
PCT Pub. Date: Jun. 1, 2017

(65) Prior Publication Data
US 2018/0370917 A1    Dec. 27, 2018

(30) Foreign Application Priority Data

Nov. 25, 2015  (JP) .................. 229882/2015
Jul. 12, 2016  (JP) .................. 137763/2016

(51) Int. Cl.
C07D 213/71 (2006.01)
C07D 213/74 (2006.01)
C07D 213/73 (2006.01)
C07D 213/76 (2006.01)
C07D 213/84 (2006.01)

(52) U.S. Cl.
CPC ......... *C07D 213/71* (2013.01); *C07D 213/73* (2013.01); *C07D 213/74* (2013.01); *C07D 213/76* (2013.01); *C07D 213/84* (2013.01)

(58) Field of Classification Search
None
See application file for complete search history.

(56) References Cited

U.S. PATENT DOCUMENTS

| | | | |
|---|---|---|---|
| 5,739,326 | A | 4/1998 | Selby et al. |
| 6,531,501 | B1 | 3/2003 | Huber et al. |
| 8,853,238 | B2 * | 10/2014 | Takyo ............... A01N 43/52 514/301 |
| 2012/0309964 | A1 | 12/2012 | Hamamoto et al. |
| 2014/0364444 | A1 | 12/2014 | Takyo et al. |

(Continued)

FOREIGN PATENT DOCUMENTS

| | | |
|---|---|---|
| CN | 10585284 | 10/2016 |
| CN | 105985284 | 10/2016 |

(Continued)

OTHER PUBLICATIONS

European Search Report issued for Application No. 16868689.7, dated Jun. 17, 2019, 8 pages.
International Search Report for PCT/JP2016/085036, dated Jan. 19, 2017, 3 pages.
Kanishchev et al., "Synthesis and Characterization of 2-Pyridylsulfur Pentafluorides", Angew. Chem. Int. Ed., 2015, 54, 280-284.
Kosobokov et al., "Importance of a Fluorine Substituent for the Preparation of meta- and para-Pentafluoro-λ(60)-sulfanyl-Substituted Pyridines", Angew. Chem. Int. Ed., 2016, vol. 55, No. 36. pp. 10781-10785.
Savoie et al., "Preparation and Utility of Organic Pentafluorosulfanyl-Containing Compounds", Chem. Rev. 2015, 115, 1130-1190.

(Continued)

*Primary Examiner* — Kamal A Saeed
(74) *Attorney, Agent, or Firm* — Adsero IP

(57) ABSTRACT

A pyridine compound having a $SF_5$ group on position-3 and position-4 of a pyridine ring is provided. Pentafluorosulfanyl pyridine represented by formula (d):

[Formula 1]

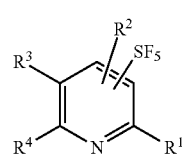

(d)

wherein a $SF_5$ group binds to either one of position-3 or position-4 of a pyridine ring, and $R^2$ binds to the other one of position-3 or position-4; and
$R^1$, $R^2$, $R^3$, and $R^4$ are independently a hydrogen atom, a halogen atom, a substituted or non-substituted alkyl group having 1 to 18 carbon atoms, a substituted or non-substituted aryl group having 6 to 30 carbon atoms, a nitro group, a cyano group, a substituted or non-substituted alkanesulfonyl group having 1 to 18 carbon atoms, a substituted or non-substituted arenesulfonyl group having 6 to 30 carbon atoms, a substituted or non-substituted alkoxy group having 1 to 18 carbon atoms, a substituted or non-substituted aryloxy group having 6 to 30 carbon atoms, an acyloxy group having 1 to 18 carbon atoms, a substituted or non-substituted alkanesulfonyloxy group having 1 to 18 carbon atoms, a substituted or non-substituted arenesulfonyloxy group having 6 to 30 carbon atoms, a substituted or non-substituted alkoxycarbonyl group having 2 to 18 carbon atoms, a substituted or non-substituted aryloxycarbonyl group having 7 to 30 carbon atoms, a substituted carbamoyl group having 2 to 18 carbon atoms, a substituted amino group having 1 to 18 carbon atoms, an amino group, an azide group, a substituted or non-substituted aralkyloxy group having 7 to 30 carbon atoms, a substituted or non-substituted aralkylsulfide group having 7 to 30 carbon atoms, or a $SF_5$ group.

9 Claims, No Drawings

(56) References Cited

U.S. PATENT DOCUMENTS

2015/0315139 A1  11/2015  Umemoto et al.
2015/0366207 A1  12/2015  Shimizu et al.

FOREIGN PATENT DOCUMENTS

| EP | 0693056 | 1/1996 |
| JP | 08-508476 | 9/1996 |
| JP | 2013-136519 | 7/2013 |
| JP | 2014-513037 | 5/2014 |
| WO | 9422817 | 10/1994 |
| WO | 2011/105506 | 9/2011 |
| WO | 2014/119674 | 8/2014 |

OTHER PUBLICATIONS

Takada et al., "Synthesis of (Chlorotetrafluore λ(6)-sulfanyl) pyridines", $39^{th}$ Japanese Symposium on Fluorine Chemistry Koen Yoshishu, Sep. 29, 2019, pp. 152-153.

Takada et al., "Synthesis and reaction of (chlorotetrafluoro λ(6)-sulfanyl) pyridines" $46^{th}$ Congress of Heterocyclic Chemistry Koen Yoshishu, Sep. 9, 2016, pp. 257-258.

* cited by examiner

PENTAFLUOROSULFANYL PYRIDINE

CROSS-REFERENCE TO RELATED APPLICATION

This application claims priority to and is a 35 U.S.C. § 371 national phase application of PCT/JP2016/085036 (WO2017/090746), filed on Nov. 25, 2016 entitled "PENTAFLUOROSULFANYL PYRIDINE", which application claims priority to and the benefit of Japanese Patent Application Nos. 229882/2015, filed Nov. 25, 2015; and 137763/2016, filed Jul. 12, 2016, the disclosures of which are incorporated herein by reference in their entirety.

TECHNICAL FIELD

The present invention relates to pentafluorosulfanyl pyridine and a manufacturing process of the same.

BACKGROUND ART

The pentafluorosulfanyl group (hereinafter referred to as the $SF_5$ group) is an electron-withdrawing and lipophilic substituent used for designing a functional organic molecule. Accordingly, a $SF_5$ group-containing compound is crucial in the development of a liquid crystal molecule or a low molecular weight medicine/agricultural chemical molecule, and the synthetic method of such compound is recently under development (NPL1). It is particularly important to introduce a $SF_5$ group to the pyridine ring, which is widely used as biologically active substances in pharmaceutical and agrochemicals, but the introduction of SF5 group is difficult, due to the instability of the intermediates, namely trifluorosulfanyl pyridine and halotetrafluorosulfanyl pyridine. Proposed as a method for introducing $SF_5$ group to pyridine ring is the one using a disulfide compound as a starting material, and the disulfide is oxidized in the presence of potassium fluoride by chlorine gas and then the subjecting obtained material, through a halogen exchange reaction using silver fluoride, is converted to the compound having a $SF_5$ group at position-2 of the pyridine ring (NPL2). However, a pragmatic method for introducing a $SF_5$ group to position-3 or position-4 of the pyridine ring has yet to be developed. Although there is report that a $SF_5$ group may be introduced to position-3 of the pyridine ring by fluorination of pyridyldisulfide using $AgF_2$ (PTL1), only a single sentence is attributed to the fact, and no data of the compound such as NMR or Examples of the compound are shown. There are also other reports of bioactive compound groups that have a $SF_5$ group introduced onto position-3 of the pyridine ring (PTL2 to PTL5), but similarly to the above, only a single sentence is attributed to the fact, and no data of the compound or Examples of the compound are shown.

There is no report of a compound having a $SF_5$ group on position-4 of a pyridine ring, and of a compound having a chlorotetrafluorosulfanyl group (hereinafter referred to as the SF4Cl group) on position-3 or position-4 of the pyridine ring.

CITATION LIST

Patent Literature

[PTL1] WO 1994/022817
[PTL2] U.S. Pat. No. 5,739,326
[PTL3] U.S. Pat. No. 6,531,501
[PTL4] WO 2011/105506
[PTL5] WO 2014/119674

Non Patent Literature

[NPL1] Chem. Rev. 2015, 115, 1130.
[NPL2] Angew. Chem. Int. Ed. 2015, 54, 280.

SUMMARY OF INVENTION

Technical Problem

The synthesis of $SF_5$-containing pyridine is extremely difficult because the intermediates are unstable, and the only case reported to have been successfully synthesized so far is a compound having a $SF_5$ group on position-2 of the pyridine ring. On the other hand, if a compound having a $SF_5$ group or its precursor, a $SF_4Cl$ group, bound to a position other than position-2 of the pyridine ring is successfully synthesized, such compound would greatly benefit the design of the next generation medicine/agricultural chemical molecule. In view of this circumstance, the present invention is directed to the issue of providing a pyridine having a $SF_5$ group or a $SF_4Cl$ group on position-3 or position-4 of the pyridine ring and a manufacturing process of the same.

Solution of Problem

The present inventors found that the above issue can be solved by using pyridyldisulfide that possesses specific substituents as a starting material, and completed the present invention. In other words, the aforementioned issue may be solved by the present invention described below.

(1) Pentafluorosulfanyl pyridine represented by formula (d) shown below, wherein a $SF_5$ group is substituted on either position-3 or position-4 of a pyridine ring.
(2) Pentafluorosulfanyl pyridine according to (1), wherein at least one of the $R^1$ and $R^4$ is a fluorine atom.
(3) Pentafluorosulfanyl pyridine according to (1) that is 2-fluoro-3-pentafluorosulfanyl pyridine, 2,6-difluoro-3-pentafluorosulfanyl pyridine, or 6-fluoro-3-pentafluorosulfanyl pyridine.
(4) Chlorotetrafluorosulfanyl pyridine represented by formula (c') shown below, wherein a $SF_4Cl$ group is substituted on either position-3 or position-4 of a pyridine ring.
(5) Chlorotetrafluorosulfanyl pyridine according to (4), wherein at least one of the $R^1$ and $R^4$ is a fluorine atom.
(6) Chlorotetrafluorosulfanyl pyridine according to (4) that is 2-fluoro-3-chlorotetrafluorosulfanyl pyridine, 2,6-difluoro-3-chlorotetrafluorosulfanyl pyridine, or 6-fluoro-3-chlorotetrafluorosulfanyl pyridine.
(7) A manufacturing process of pentafluorosulfanyl pyridine according to (1) comprising: a step of reacting pyridyldisulfide represented by formula (a) shown below with halogens selected from a group consisting of chlorine, bromine, iodine and a halogen compound, and a fluoride salt represented by formula (b) shown below to form halotetrafluorosulfanyl pyridine represented by formula (c) shown below; and a step of reacting the obtained halotetrafluorosulfanyl pyridine with a fluoride source to form pentafluorosulfanyl pyridine.
(8) The process according to (7), wherein a halogen to be reacted with the pyridyldisulfide compound is chlorine ($Cl_2$).
(9) The process according to (7), wherein the fluoride salt represented by formula (b) is alkali metal fluoride.

(10) The process according to any one of (7) to (9), wherein the fluoride source is hydrogen fluoride.

Advantageous Effect of Invention

The present invention may provide manufacturing of a pentafluorosulfanyl pyridine in which position-3 or position-4 of the pyridine ring is substituted with a SF5 group and a manufacturing process of this compound.

DESCRIPTION OF EMBODIMENTS

The present invention is described in detail below. In this invention, the expression "X to Y" includes the values on both ends, that is, X and Y.
1. Pentafluorosulfanyl Pyridine
The pentafluorosulfanyl pyridine of the present invention is represented by formula (d).

[Formula 1]

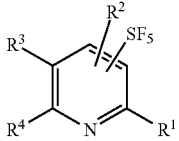

(d)

wherein the $SF_5$ group binds to the pyridine ring at position-3 or position-4. $R^2$ binds to one of position-3 and position-4 that the $SF_5$ group does not bind to.

$R^1$, $R^2$, $R^3$, and $R^4$ are substituents on the pyridine ring, which are independently a hydrogen atom, a halogen atom, a substituted or non-substituted alkyl group having 1 to 18 carbon atoms, a substituted or non-substituted aryl group having 6 to 30 carbon atoms, a nitro group, a cyano group, a substituted or non-substituted alkanesulfonyl group having 1 to 18 carbon atoms, a substituted or non-substituted arenesulfonyl group having 6 to 30 carbon atoms, a substituted or non-substituted alkoxy group having 1 to 18 carbon atoms, a substituted or non-substituted aryloxy group having 6 to 30 carbon atoms, a substituted or non-substituted acyloxy group having 1 to 18 carbon atoms, a substituted or non-substituted alkanesulfonyloxy group having 1 to 18 carbon atoms, a substituted or non-substituted arenesulfonyloxy group having 6 to 30 carbon atoms, a substituted or non-substituted alkoxycarbonyl group having 2 to 18 carbon atoms, a substituted or non-substituted aryloxycarbonyl group having 7 to 30 carbon atoms, a substituted carbamoyl group having 2 to 18 carbon atoms, a substituted amino group having 1 to 18 carbon atoms, an amino group, an azide group, a substituted or non-substituted aralkyloxy group having 7 to 30 carbon atoms, a substituted or non-substituted aralkylsulfide group having 7 to 30 carbon atoms, or a $SF_5$ group. The halogen atoms are a fluorine atom, a chlorine atom, a bromine atom, or an iodine atom. A substituted or non-substituted aralkyloxy group having 7 to 30 carbon atoms include a benzyloxy group ($Ph-CH_2-O-$) or a substituted benzyloxy group. A substituted or non-substituted aralkylsulfide group having 7 to 30 carbon atoms include a benzylsulfide group ($Ph-CH_2-S-$) or a substituted benzylsulfide group. A substituted amino group having 1 to 18 carbon atoms include a benzylamino group or a substituted benzylamino group.

Due to the availability of the halotetrafluorosulfanyl compound, which is a precursor of Compound (d), $R^1$ and $R^2$ should preferably be a hydrogen atom or a fluorine atom, which exhibit low steric hindrance.

In view of the stability of the halotetrafluorosulfanyl compound, which is a precursor of Compound (d), at least one of $R^1$ and $R^4$ should preferably be a halogen atom.

In addition, at least one of $R^1$ and $R^4$ should preferably be a substituted amino group having 1 to 18 carbon atoms, an amino group, an azide group, a substituted or non-substituted aralkyloxy group having 7 to 30 carbon atoms, or a substituted or non-substituted aralkylsulfide group having 7 to 30 carbon atoms.
2. Chlorotetrafluorosulfanyl Pyridine
The chlorotetrafluorosulfanyl pyridine of the present invention is represented by formula (c').

[Formula 2]

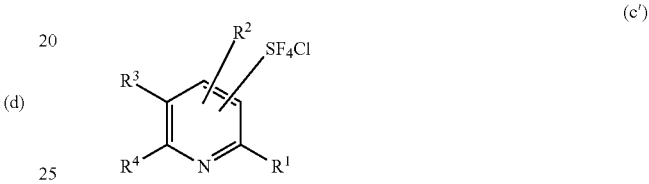

(c')

wherein $SF_4Cl$ group is a group that provides the $SF_5$ group to Compound (d). $R^2$, $R^3$, and $R^4$ are defined in the same manner as Compound (d).
3. Manufacturing Process of Pentafluorosulfanyl Pyridine
It is preferable for pentafluorosulfanyl pyridine to be manufactured by the following scheme.

[Formula 3]

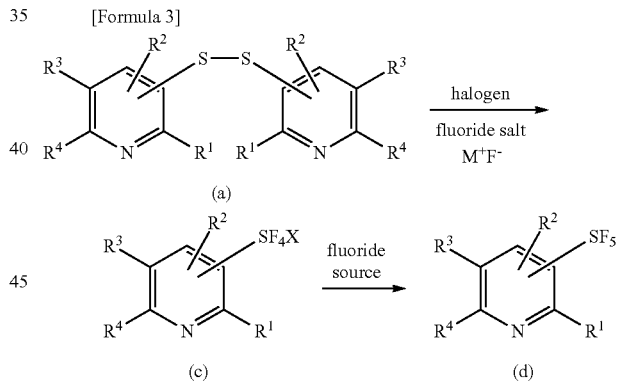

(1) Synthesis of Halotetrafluorosulfanyl Pyridine (c)
The pyridyldisulfide compound represented by formula (a) is reacted with halogens selected from a group consisting of chlorine, bromine, iodine and interhalogen compounds, and a fluoride salt represented by formula (b) to manufacture halotetrafluorosulfanyl pyridine compound represented by formula (c).

Specifically speaking, the pyridyldisulfide compound (Compound (a)) is first reacted with a fluoride salt under the presence of halogens to obtain halotetrafluorosulfanyl pyridine (Compound (c)). The amount of halogens used may be any amount as long as it is excessive against the pyridyldisulfide compound, but an amount of 12 to 16 equivalents is preferred. The amount of fluoride salt to be used may be any amount as long as it is excessive against pyridyldisulfide, but an amount of 14 to 18 equivalents is preferred. There is no limitation to the solvent, but an aprotic, polar solvent, such as acetonitrile, is preferred in view of the solubility of the fluoride salt and to prevent the fluoride salt's reaction with halogens. The reaction temperature may be adjusted as necessary, but a temperature of −20 to 50° C. is preferred. The reaction time is not limited, but it may be from a few hours to a few days, preferably 2 to 3 days. The reaction container is preferably that made from fluoropolymer, such as polytetrafluoroethylene, in order to suppress secondary reactions. In addition, the reaction should preferably be performed under a deoxidized atmosphere and a dry condition in view of the instability of the reaction intermediates.

The $R^1$, $R^2$, $R^3$, and $R^4$ in Compound (d) may differ from $R^1$, $R^2$, $R^3$, and $R^4$ of the starting material, Compound (a). Accordingly, some embodiments of the present invention includes transforming $R^1$, $R^2$, $R^3$, and $R^4$ to a different $R^1$, $R^2$, $R^3$, and $R^4$. This transformation may be performed in a reaction that converts Compound (a) to Compound (c) or in a reaction that transforms Compound (c) to Compound (d).

Typical halogens to be used in the present invention include chlorine ($Cl_2$), bromine ($Br_2$), iodine ($I_2$), and interhalogen compounds such as ClF, BrF, ClBr, ClI, $Cl_3I$, BrI. Chlorine ($Cl_2$) is preferable from the cost perspective.

The fluoride salt represented by formula (b) is easily acquired, and examples of such fluoride salt include metal fluorides, ammonium fluorides and phosphonium fluorides. Examples of preferable metal fluorides are alkali metal fluorides, such as lithium fluoride, sodium fluoride, potassium fluoride (including spray-dried potassium fluoride), rubidium fluoride, and caesium fluoride. Examples of preferable ammonium fluorides are tetramethyl ammonium fluoride, tetrabutyl ammonium fluoride, benzyltrimethyl ammonium fluoride, and benzyltriethyl ammonium fluoride. Examples of preferable phosphonium fluorides are tetramethyl phosphonium fluoride, tetraethyl phosphonium fluoride, tetrapropyl phosphonium fluoride, tetrabutyl phosphonium fluoride, tetraphenyl phosphonium fluoride, and tetratolylphosphonium fluoride. An alkali metal fluoride such as potassium fluoride and caesium fluoride are preferred from the perspective of ease of acquisition and of capacity to provide high yield, and potassium fluoride is preferred from the cost perspective.

A mixture of metal fluoride and ammonium fluoride or phosphonium fluoride, a mixture of ammonium fluoride and phosphonium fluoride, and a mixture of metal fluoride, ammonium fluoride and phosphonium fluoride may be used as a fluoride salt represented by formula (b).

(2) Synthesis of Pentafluorosulfanyl Pyridine (d)

Halotetrafluorosulfanyl pyridine represented by formula (c) is reacted with a fluoride source to obtain pentafluorosulfanyl represented by formula (d).

Specifically speaking, halotetrafluorosulfanyl pyridine (Compound (c)) is reacted with a fluoride source to obtain pentafluorosulfanyl pyridine (Compound (d)) by a halogen exchange reaction. The amount of fluoride source used may be any amount as long as it is excessive against pyridyldisulfide, but an amount of 12 to 16 equivalents is preferred. The amount of fluoride source to be used may be any amount as long as it is excessive against halotetrafluorosulfanyl pyridine, but an amount of 1 to 3 equivalents is preferred. A solvent-less reaction is preferred from the perspective of high reaction efficiency and low cost, but a halogen-containing carbon compound, ether, nitrile (acetonitrile, etc.), or nitro compound may also be used as a solvent to adjust reactivity. The reaction temperature may be adjusted as necessary, but a temperature of −100 to 150° C. is preferred. The reaction time is not limited, but it may be from a few hours to a few days, preferably 2 to 3 days. The reaction container is preferably that made from fluoropolymer, such as polytetrafluoroethylene, in order to suppress secondary reactions. In addition, the reaction should preferably be performed under a deoxidized atmosphere and a dry condition from the perspective of instability of reaction intermediates.

The fluoride source to be used is an anhydride compound exhibiting an activity of fluorinating halotetrafluorosulfanyl pyridine represented by formula (c). The fluoride source may be selected from a fluoride of a typical element in the periodic table, a fluoride or a transition element in the periodic table, and a mixture or a compound of fluorides of the typical element or the transition element. The fluoride source may be hydrogen fluoride or a mixture, salt or complex with a single or multiple types of organic molecules that does not limit the present invention. The fluoride source also includes a mixture or a compound of the fluoride source and a fluoride source-activating compound, such as $SbCl_5$, $AlCl_3$, $PCl_5$, $BCl_3$. Fluorides of the Group 11 elements (Cu, Ag, Au) and Group 12 elements (Zn, Cd, Hg), which are transition metal fluorides, are preferred from the perspective of high reactivity of halogen exchange.

The present process is categorized into reactions performed in stages as shown below. 1) Oxidation of the sulfur atom binding to position-3 or position-4 of the pyridine ring by halogen and fluoride salt, and generation of halotetrafluorosulfanyl compound by halogen exchange. 2) Generation of pentafluorosulfanyl pyridine compound by halogen exchange.

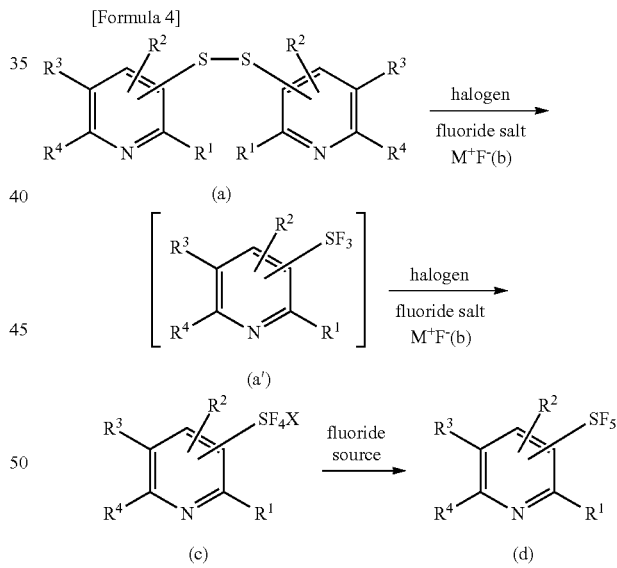

In Stage 1) above, a compound including a $SF_3$ group represented by formula (a') is provided as an intermediate. The compound is a tetravalent sulfur compound, and its presence may be verified by $^{19}F$-NMR. A pyridine compound possessing a $SF_3$ group or a $SF_4Cl$ group is easily decomposed by a nucleophilic attack by water or an anion type in the system. As such, $R^1$ or $R^4$ that is a halogen atom improves the chemical stability of pyridyldisulfide such that this reaction may be carried out more efficiently.

By reacting pentafluorosulfanyl pyridine (d), whose $R^1$ or $R^4$ is a halogen atom, with a nucleophilic reagent, it is possible to substitute $R^1$ or $R^4$ with another functional group.

The scheme of the present invention and an example of the thus synthesized pentafluorosulfanyl pyridine (d) is shown below.

[Formula 5]

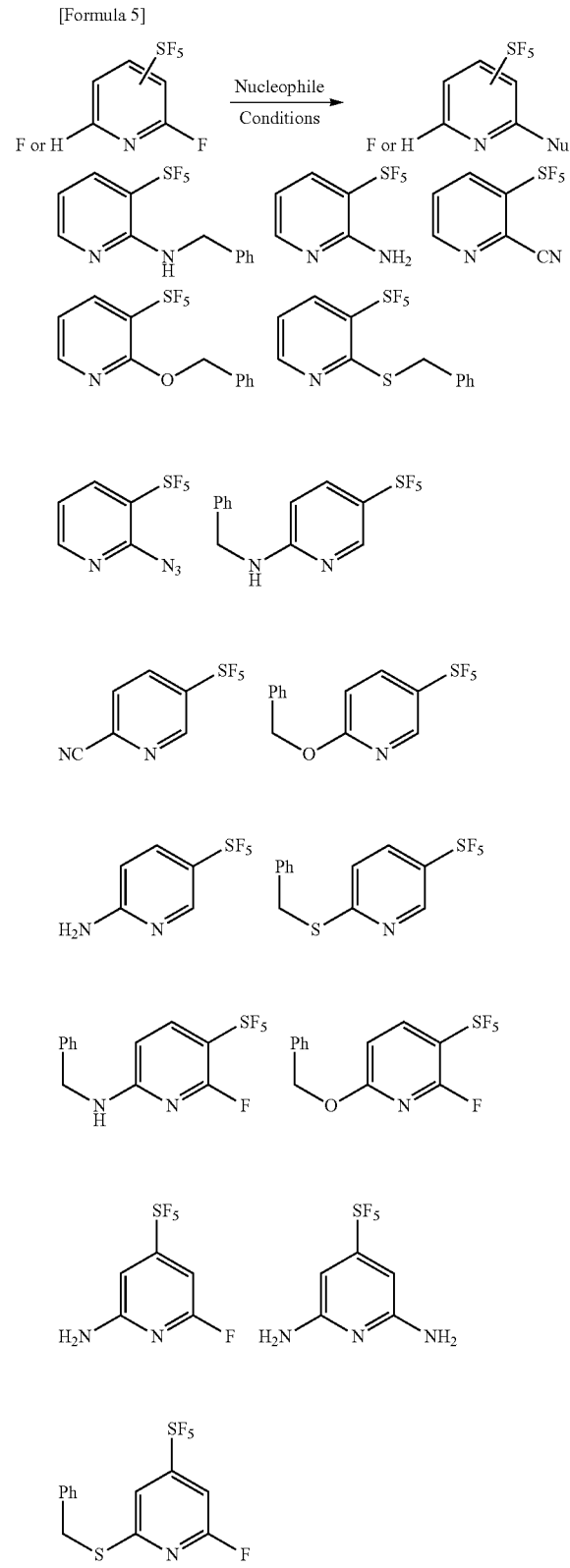

EXAMPLES

Example 1

The following reaction was performed to synthesize a pentafluorosulfanyl pyridine compound.

[Formula 6]

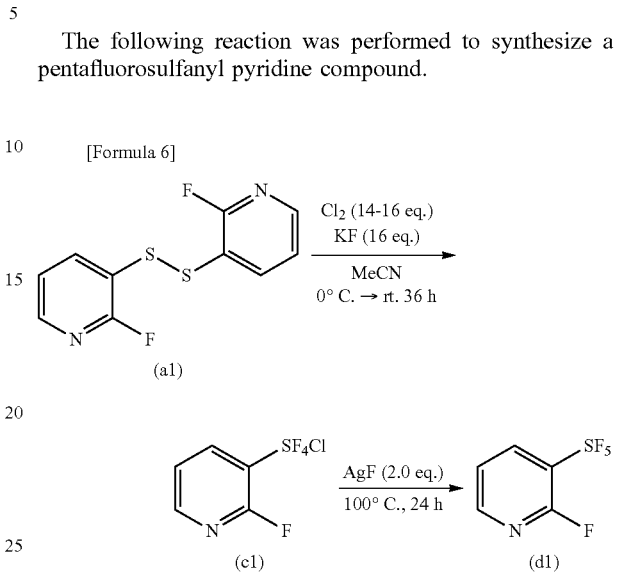

Potassium fluoride (spray-dried product, 2.32 g, 40 mmol, Wako pure chemical corp.) and acetonitrile (15 mL) were put in a 30 mL polytetrafluoroethylene container under a nitrogen atmosphere. The agitated mixture was cooled in an ice-containing water bath, and a polytetrafluoroethylene tube (inner diameter 1 mm) was used to perform bubbling of chlorine ($Cl_2$; about 2.5 g to 2.8 g, about 35 to 40 mmol) in the mixture for 10 min at an outlet pressure of 0.005 MPa. Then, pyridyldisulfide (a1) (641 mg, 2.5 mmol) synthesized by the inventors was added under a nitrogen gas flow, and the container was sealed to perform agitation at room temperature for 36 h. After the reaction completed, the insoluble matter was removed under a nitrogen atmosphere using a glass filter. The filtrate was evaporated in a polytetrafluoroethylene container under vacuum, and the obtained residue (2-fluoro-3-chlorotetrafluorosulfanyl pyridine (c1)) was used for the subsequent reaction without being purified.

To the 2-fluoro-3-chlorotetrafluorosulfanyl pyridine (c1) in the 30 mL polytetrafluoroethylene container, obtained in the previous step, was added silver fluoride (I) (634 mg, 5.0 mmol), and the mixture was agitated under a nitrogen atmosphere at 100° C. for 24 h. After cooling to room temperature, water (5 mL) and dichloromethane (5 mL) were added to the mixture, and the mixture was agitated for 1 h., then, the product was extracted using dichloromethane and the organic phase was dried by sodium sulfate. Then, the solvent was removed by distillation under reduced pressure, and purified by silica gel column chromatography (pentane/dichloromethane=5/1→2/1, Rf value 0.56) and a transparent, oil-like product (d1) (151 mg, 27%) was obtained.

Similar syntheses were performed using the following compounds. The analysis result using mass spectrometry and NMR is summarized below. Mass spectrometry was performed in the present invention using a device by Shimadzu corporation with a serial name of LCMS-2020, and $^1$H-NMR and $^{19}$F-NMR were performed using Mercury 300 by Varian.

TABLE 1

EXAMPLE 1

| Pyridyldisulfide | | Chlorotetrafluorosulfanyl Pyridine | | Pentafluorosulfanyl Pyridine | |
|---|---|---|---|---|---|
| [structure] | a1 | [structure] SF₄Cl | c1 | [structure] SF₅ 24% yield | d1 |
| [structure] | a2 | [structure] SF₄Cl | c2 | [structure] SF₅ 27% yield | d2 |
| [structure] | a3 | [structure] SF₄Cl | c3 | [structure] SF₅ 20% yield | d3 |

[Formula 7]

3-(Chlorotetrafluorosulfanyl)-2-fluoropyridine (c1)

$^1$H NMR (CDCl$_3$, 300 MHz): δ=7.36 (dd, J=6.5, 5.5 Hz, 1H), 8.20 (td, J=8.3, 1.7 Hz, 1H), 8.40 (d, J=4.5 Hz, 1H); $^{19}$F NMR (CDCl$_3$, 300 MHz): δ=−59.56-−60.48 (m, 1F) 138.71 (d, J=21.5 Hz, 4F)

3-(Chlorotetrafluorosulfanyl)-2,6-difluoropyridine (c2)

$^{19}$F NMR (CDCl$_3$, 300 MHz): δ=−61.86 (s, 1F), −60.32-−61.06 (m, 1F), 139.13 (d, J=21.8 Hz, 4F)

5-(Chlorotetrafluorosulfanyl)-2-fluoropyridine (c3)

$^{19}$F NMR (CDCl$_3$, 300 MHz): δ=−63.88 (s, 1F), 136.28 (s, 4F)

2-Fluoro-3-(pentafluorosulfanyl)pyridine (d1)

MS (EI, m/z) 223 (M$^+$); $^1$H NMR (CDCl$_3$, 300 MHz): δ=7.42-7.30 (m, 1H), 8.26-8.13 (m, 1H), 8.40 (d, J=3.2 Hz, 1H); $^{19}$F NMR (CDCl$_3$, 300 MHz): δ=−60.21-−61.04 (m, 1F), 66.93 (dd, J=151.8, 24.0 Hz, 4F), 80.60-77.84 (m, 1F); (2 steps) 24% yield 2,6-Difluoro-3-(pentafluorosulfanyl)pyridine (d2)

MS (EI, m/z) 241 (M$^+$); $^1$H NMR (CDCl$_3$, 300 MHz): δ=2 6.99 (d, J=8.6 Hz, 1H), 8.51-8.06 (m, 1H); $^{19}$F NMR (CDCl$_3$, 300 MHz): δ=−63.13 (s, 1F), −61.48-−62.07 (m, 1F), 64.79 (ddd, J=150.9, 24.1, 3.6, 4F), 77.26-74.64 (m, 1F); (2 steps) 27% yield 2-Fluoro-5-(pentafluorosulfanyl)pyridine (d3)

MS (EI, m/z) 223 (M$^+$); $^1$H NMR (CDCl$_3$, 300 MHz): δ=7.07 (d, J=8.9 Hz, 1H), 8.19 (ddt, J=9.1, 6.5, 2.5 Hz, 1H), 8.70-8.62 (br, 1H); $^{19}$F NMR (CDCl$_3$, 300 MHz): δ=−61.77 (s, 1F), 65.75 (d, J=151.4 Hz, 4F), 82.97-80.04 (m, 1F); (2 steps) 20% yield Example 2

A pentafluorosulfanyl pyridine compound was synthesized by the following reaction.

[Formula 8]

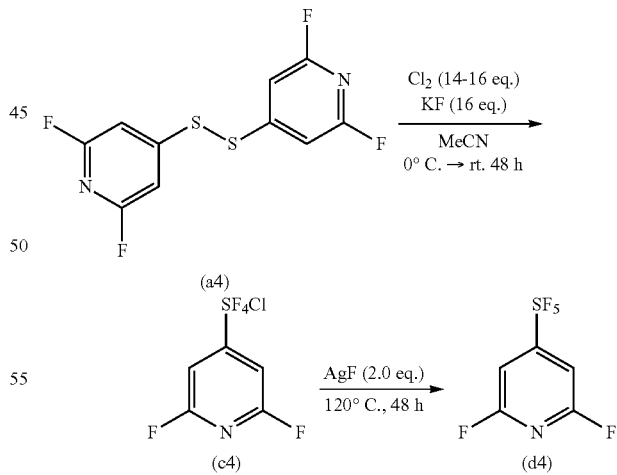

Potassium fluoride (spray-dried product, 6.03 g, 104 mmol, Wako pure chemical corp.) and acetonitrile (39 mL) were put under a nitrogen atmosphere in a 60 mL polytetrafluoroethylene container. The agitated mixture was cooled in an ice-containing water bath, and a polytetrafluoroethylene tube (inner diameter 1 mm) was used to bubble chlorine (Cl$_2$; about 6.5 g to 7.4 g, about 91 to 104 mmol) in the mixture for 10 min at an outlet pressure of 0.005 MPa. Then, pyridyldisulfide (a4) (1.90 g, 6.5 mmol) synthesized by the inventors was added under a nitrogen gas flow, and the container was sealed to perform agitation at room temperature for 48 h. After the reaction completed, the insoluble matter was removed under a nitrogen atmosphere using a glass filter. The filtrate was evaporated in a polytetrafluoroethylene container under vacuum, and the obtained residue (2,6-difluoro-4-chlorotetrafluorosulfanyl pyridine (c4), 3.01 g, 90% yield) was used for the subsequent reaction without being purified.

To the previously obtained 2,6-difluoro-4-chlorotetrafluorosulfanyl pyridine (c4) (2.58 g, 10 mmol) in the 30 mL polytetrafluoroethylene container was added silver fluoride (I) (2.54 g, 20 mmol), and the mixture was agitated under a nitrogen atmosphere at 120° C. for 48 h. After cooling to room temperature, water (10 mL) and dichloromethane (10 mL) were added to the mixture, and the mixture was agitated for 1 h., then, the product was extracted using dichloromethane and the organic phase was dried by sodium sulfate. Then, the solvent was removed by distillation under reduced pressure, and purified by silica gel column chromatography (pentane/dichloromethane=20/1, Rf value 0.34) and a transparent, oil-like product (d4) (844 mg, 35% yield) was obtained.

A similar synthesis was further performed and product (d5) was obtained. The analysis result using mass spectrometry and NMR is summarized below.

[Formula 9]

4-(Chlorotetrafluorosulfanyl)-2,6-difluoropyridine (c4)

$^1$H NMR (300 MHz, CDCl$_3$) δ: 7.20 (s, 2H). $^{19}$F NMR (282 MHz, CDCl$_3$) δ: 132.28 (s, 4F), −63.35 (s, 2F); 90% yield 4-(Chlorotetrafluorosulfanyl)-2-fluoropyridine (c5)

NMR (300 MHz, CDCl$_3$) δ: 8.42 (d, J=4.7 Hz, 1H), 7.53 (d, J=4.7 Hz, 1H), 7.29 (s, 1H). $^{19}$F NMR (282 MHz, CDCl$_3$) δ: 132.48 (s, 4F), −63.54 (s, 1F); 68% yield 2,6-Difluoro-4-(pentafluorosulfanyl)pyridine (d4)

HRMS (TOF/EI+): Calculated for C$_5$H$_2$F$_7$NS$^+$: 240.9796, found: 240.9799; $^1$H NMR (300 MHz, CDCl$_3$) δ: 7.22 (s, 2H). $^{19}$F NMR (282 MHz, CDCl$_3$) δ: 78.69-75.66 (m, 1F), 60.91 (d, J=152.4 Hz, 4F), −63.14 (s, 2F). $^{13}$C NMR (125 MHz, CDCl$_3$) δ: 167.1-166.4 (m), 161.7 (dd, J=250.8, 15.3 Hz), 105.0-104.4 (m); 35% yield

TABLE 2

Example 2

| Pyridyldisulfide | | Chlorotetrafluorosulfanyl Pyridine | | Pentafluorosulfanyl Pyridine | |
|---|---|---|---|---|---|
| [2,6-difluoropyridyl disulfide structure] | a4 | [SF$_4$Cl-2,6-difluoropyridine structure] 90% yield | c4 | [SF$_5$-2,6-difluoropyridine structure] 35% yield | d4 |
| [2-fluoropyridyl disulfide structure] | a5 | [SF$_4$Cl-2-fluoropyridine structure] 68% yield | c5 | [SF$_5$-2-fluoropyridine structure] 5% yield | d5 |

2-Fluoro-4-(pentafluorosulfanyl)pyridine (d5)

HRMS (TOF/EI+): Calculated for $C_5H_3F_6NS^+$: 222.9890, found: 222.9888;
$^1$H NMR (300 MHz, CDCl$_3$) δ: 8.44 (d, J=5.4 Hz, 1H), 7.56 (d, J=5.4 Hz, 1H), 7.37-7.24 (m, 1H). $^{19}$F NMR (282 MHz, CDCl$_3$) δ: 79.85-76.24 (m, 1F), 60.52 (d, J=151.7 Hz, 4F), −63.43 (s, 1F). $^{13}$C NMR (125 MHz, CDCl$_3$) δ: 163.8 (pd, J=20.8, 7.5 Hz), 163.8 (d, J=242.6 Hz), 149.2 (d, J=15.0 Hz), 118.2-118.0 (m), 107.8 (dp, J=42.4, 4.9 Hz); 5% yield

Example 3

Pentafluorosulfanyl pyridine (d1) synthesized as described above was subjected to a nucleophilic substitution reaction. Table 3 shows the nucleophilic reagent, the reaction condition and the product.

TABLE 3

Example 3: Nucleophilic substitution reaction of Compound (d1)

| Nucleophilic Reagent | Reaction Condition | Product (number shows yield) |
|---|---|---|
| benzylamine | 95° C., 10 h. | 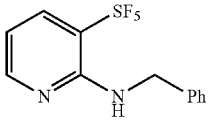 86% |
| NH$_3$ | 105° C., 18 h. |  72% |
| Me$_3$SiCN | 55° C., 10 h. | 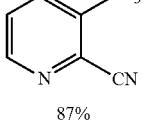 87% |
| benzylalcohol | 95° C., 10 h. | 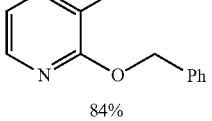 84% |
| benzylthiol | 95° C., 10 h. | 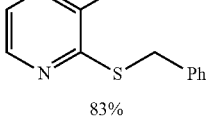 83% |
| NaN$_3$ | 95° C., 10 h. | 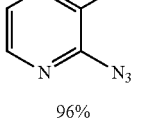 96% |

Example 4

Pentafluorosulfanyl pyridine (d3) synthesized as described above was subjected to a nucleophilic substitution reaction. Table 4 shows the nucleophilic reagent, the reaction condition, and the product, etc.

TABLE 4

Example 4: Nucleophilic substitution reaction of Compound (d3)

| Nucleophilic Reagent | Reaction Condition | Product (number shows yield) |
|---|---|---|
| benzylamine | 95° C., 10 h. | 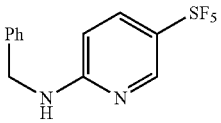 92% |
| Me$_3$SiCN | 55° C., 10 h. | 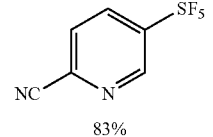 83% |
| benzylalcohol | 95° C., 10 h. | 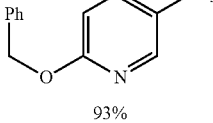 93% |
| NH$_3$ | 105° C., 18 h. | 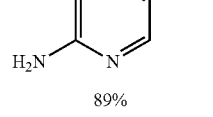 89% |
| benzylthiol | 95° C., 10 h. | 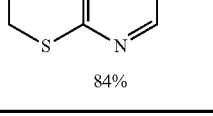 84% |

Example 5

Pentafluorosulfanyl pyridine (d2) synthesized as described above was subjected to a nucleophilic substitution reaction. Table 5 shows the nucleophilic reagent, the reaction condition, and the product, etc.

TABLE 5

Example 5: Nucleophilic substitution reaction of Compound (d2)

| Nucleophilic Reagent | Reaction Condition | Product (number shows yield) |
|---|---|---|
| benzylamine | 25° C., 10 h. | 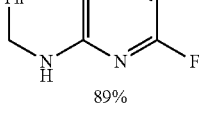 89% |

TABLE 5-continued

Example 5: Nucleophilic substitution reaction of Compound (d2)

| Nucleophilic Reagent | Reaction Condition | Product (number shows yield) |
|---|---|---|
| benzylalcohol | 25° C., 10 h. | 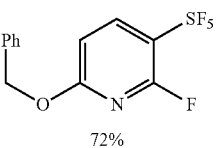 72% |

Example 6

Pentafluorosulfanyl pyridine (d4) synthesized as described above was subjected to a nucleophilic substitution reaction. Table 6 shows the nucleophilic reagent, the reaction condition, and the product, etc.

TABLE 6

Example 6: Nucleophilic substitution reaction of Compound (d4)

| Nucleophilic Reagent | Reaction Condition | Product (number shows yield) |
|---|---|---|
| $NH_3$ | 90° C., 3 h. | 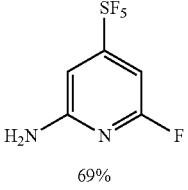 69% |
| $NH_3$ | 120° C., 24 h. | 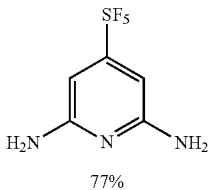 77% |
| benzylthiol | 95° C., 10 h. | 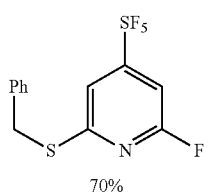 70% |

It is apparent that a pyridine compound having a pentafluorosulfanyl group at position-3 and position-4 are obtained by the present invention. A pyridine compound having a halogen atom together with pentafluorosulfanyl group may be synthesized in the present invention, and modification such as a coupling reaction, performed using the halogen atom, allows the invention to be of assistance in the synthesis of physiological substances such as medicine.

The invention claimed is:

1. Pentafluorosulfanyl pyridine represented by formula (d):

[Formula 1]

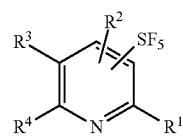

(d)

wherein a $SF_5$ group binds to either one of position-3 or position-4 of a pyridine ring, and $R^2$ binds to the other one of position-3 or position-4; and $R^1$, $R^2$, $R^3$, and $R^4$ are independently a hydrogen atom, a halogen atom, a substituted or non-substituted alkyl group having 1 to 18 carbon atoms, a substituted or non-substituted aryl group having 6 to 30 carbon atoms, a nitro group, a cyano group, a substituted or non-substituted alkanesulfonyl group having 1 to 18 carbon atoms, a substituted or non-substituted arenesulfonyl group having 6 to 30 carbon atoms, a substituted or non-substituted alkoxy group having 1 to 18 carbon atoms, a substituted or non-substituted aryloxy group having 6 to 30 carbon atoms, an acyloxy group having 1 to 18 carbon atoms, a substituted or non-substituted alkanesulfonyloxy group having 1 to 18 carbon atoms, a substituted or non-substituted arenesulfonyloxy group having 6 to 30 carbon atoms, a substituted or non-substituted alkoxycarbonyl group having 2 to 18 carbon atoms, a substituted or non-substituted aryloxycarbonyl group having 7 to 30 carbon atoms, a substituted carbamoyl group having 2 to 18 carbon atoms, a substituted amino group having 1 to 18 carbon atoms, an amino group, an azide group, a substituted or non-substituted aralkyloxy group having 7 to 30 carbon atoms, a substituted or non-substituted aralkylsulfide group having 7 to 30 carbon atoms, or a $SF_5$ group), wherein at least one of the $R^1$ and $R^4$ is a fluorine atom.

2. Pentafluorosulfanyl pyridine according to claim 1 that is 2-fluoro-3-pentafluorosulfanyl pyridine, 2,6-difluoro-3-pentafluorosulfanyl pyridine, or 6-fluoro-3-pentafluorosulfanyl pyridine.

3. Chlorotetrafluorosulfanyl pyridine represented by formula (c'):

[Formula 2]

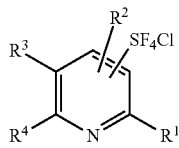

(c')

wherein a $SF_4Cl$ group binds to either one of position-3 or position-4 of a pyridine ring, and $R^2$ binds to the other one of position-3 or position-4; and R$^1$, R$^2$, R$^3$, and R$^4$ are independently a hydrogen atom, a halogen atom, a substituted or non-substituted alkyl group having 1 to 18 carbon atoms, a substituted or non-substituted aryl group having 6 to 30 carbon atoms, a nitro group, a cyano group, a substituted or non-substituted alkanesulfonyl group having 1 to 18 carbon atoms, a substituted or non-substituted arenesulfonyl group having 6 to 30 carbon atoms, a substituted or non-substituted alkoxy group having 1 to 18 carbon atoms, a substituted or non-substituted aryloxy group having 6 to 30 carbon atoms, an acyloxy group having 1 to 18 carbon atoms, a substituted or non-substituted alkanesulfonyloxy group having 1 to 18 carbon atoms, a substituted or non-substituted allenesulfonyloxy group having 6 to 30 carbon atoms, a substituted or non-substituted alkoxycarbonyl group having 2 to 18 carbon atoms, a substituted or non-substituted aryloxycarbonyl group having 7 to 30 carbon atoms, a substituted carbamoyl group having 2 to 18 carbon atoms, a substituted amino group having 1 to 18 carbon atoms, an amino group, an azide group, a substituted or non-substituted aralkyloxy group having 7 to 30 carbon atoms, a substituted or non-substituted aralkylsulfide group having 7 to 30 carbon atoms, or a SF$_5$ group).

4. Chlorotetrafluorosulfanyl pyridine according to claim 3, wherein at least one of the R$^1$ and R$^4$ is a fluorine atom.

5. Chlorotetrafluorosulfanyl pyridine according to claim 3 that is 2-fluoro-3-chlorotetrafluorosulfanyl pyridine, 2,6-difluoro-3-chlorotetrafluorosulfanyl pyridine, or 6-fluoro-3-chlorotetrafluorosulfanyl pyridine.

6. A manufacturing process of pentafluorosulfanyl pyridine according to claim 1 comprising:
a step of reacting a pyridyldisulfide compound represented by formula (a):

[Formula 3]

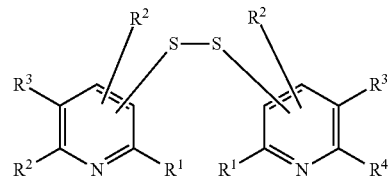

(a)

wherein R$^1$, R$^2$, R$^3$, and R$^4$ are as defined above,
with halogens selected from a group consisting of chlorine, bromine, iodine and a halogen compound, and
a fluoride salt represented by formula (b):

M$^+$F$^-$     (b)

wherein M is a metal atom, an ammonium group or a phosphonium group
to form halotetrafluorosulfanyl pyridine represented by formula (c):

[Formula 4]

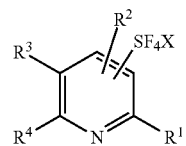

(c)

wherein R$^1$, R$^2$, R$^3$, and R$^4$ are as defined above, and X is a chlorine atom, a bromine atom or an iodine atom; and
a step of reacting the halotetrafluorosulfanyl pyridine with a fluoride source to form pentafluorosulfanyl pyridine.

7. The process according to claim 6, wherein a halogen to be reacted with pyridyldisulfide is chlorine (Cl$_2$).

8. The process according to claim 6, wherein the fluoride salt represented by formula (b) is alkali metal fluoride.

9. The process according to claim 6, wherein the fluoride source is hydrogen fluoride.

* * * * *